United States Patent
Oishi et al.

(10) Patent No.: US 7,156,240 B2
(45) Date of Patent: Jan. 2, 2007

(54) FILTER FOR PROCESSING BLOOD AND PROCESS FOR PRODUCING THE SAME

(75) Inventors: Teruhiko Oishi, Miyazaki (JP); Morikazu Miura, Oita (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 341 days.

(21) Appl. No.: 10/470,291

(22) PCT Filed: Jan. 29, 2002

(86) PCT No.: PCT/JP02/00653

§ 371 (c)(1),
(2), (4) Date: Jan. 9, 2004

(87) PCT Pub. No.: WO02/060557

PCT Pub. Date: Aug. 8, 2002

(65) Prior Publication Data

US 2004/0104165 A1    Jun. 3, 2004

(30) Foreign Application Priority Data

Jan. 29, 2002   (JP)   .............. 2001-019829

(51) Int. Cl.
B01D 29/05   (2006.01)
B01D 39/00   (2006.01)
B01D 39/16   (2006.01)
B01D 59/22   (2006.01)
B01D 67/00   (2006.01)

(52) U.S. Cl. ............ 210/490; 210/483; 210/500.1; 210/507; 210/643; 427/244

(58) Field of Classification Search ........... 210/488, 210/489, 490, 491, 503, 504, 505, 506, 507, 210/643, 483, 500.1; 427/244; 422/244
See application file for complete search history.

(56) References Cited

U.S. PATENT DOCUMENTS

| 4,936,998 | A | * | 6/1990 | Nishimura et al. |
| 5,288,403 | A | * | 2/1994 | Ohno |
| 5,547,576 | A | * | 8/1996 | Onishi et al. |
| 5,647,985 | A | * | 7/1997 | Ung-Chhun et al. |
| 6,977,044 | B1 | * | 12/2005 | Oishi et al. ............ 210/500.42 |

FOREIGN PATENT DOCUMENTS

| EP | 0606646 A1 | * | 7/1994 |
| EP | 1018346 | * | 7/2000 |
| JP | 7-25776 | * | 1/1995 |
| JP | 8-281100 | * | 10/1996 |
| JP | 11-206876 | * | 8/1999 |
| JP | 2000-51623 | * | 2/2000 |

* cited by examiner

OTHER PUBLICATIONS

Patent Abstracts of Japan, Publication No. 2000197814 A (2000).*

*Primary Examiner*—John Kim
(74) *Attorney, Agent, or Firm*—Young & Thompson

(57) ABSTRACT

A filter for reducing leukocytes and platelets from an erythrocyte preparation or a whole blood preparation which is characterized by having a filter base coated with a polymer, the content of the polymer being from 0.5 to 10 mg/m² per unit area of the total surface of the filter base, and the polymer containing 20% or less of low-molecular weight components having a molecular weight not more than ¼ of the peak top molecular weight in the gel permeation chromatogram.

8 Claims, 3 Drawing Sheets

FILTER FOR PROCESSING BLOOD AND PROCESS FOR PRODUCING THE SAME

TECHNICAL FIELD

The present invention relates to a filter for processing blood. More specifically, the present invention relates to a filter for reducing leukocytes and platelets from an erythrocyte preparation or a whole blood preparation at the same time, and to a process for producing the filter.

BACKGROUND ART

In the field of blood transfusion, in addition to whole blood transfusion using a whole blood preparation prepared by adding an anti-coagulating agent to blood collected from a donor, blood component transfusion infusing only blood components necessary for the blood recipient separated from a whole blood preparation has been commonly practiced. The blood component transfusion is classified into erythrocyte transfusion, platelet transfusion, plasma transfusion, and the like according to the blood component required by the blood recipient. As the blood component preparation used for blood component transfusion, an erythrocyte preparation, a platelet preparation, a blood plasma preparation, and the like can be given.

In recent years, leukocyte-free blood transfusion in which leukocytes contained in a blood preparation are removed in advance is applied to the whole blood transfusion and blood component transfusion. This is because of a recent discovery that the leukocytes in the preparations induce side effects of blood transfusion such as headache, nausea, chills, anhemolytic exothermic reaction, alloantigen sensitization, GVHD, and virus infection. Therefore, it is necessary to reduce leukocytes in the blood preparation to a level low enough to prevent these side effects.

On the other hand, an erythrocyte preparation may include platelets that partly migrate during a centrifuge operation. Since an anhemolytic side effect that is suspected to have been caused by platelets has been reported, it is desirable to reduce platelets to a level as low as possible. Furthermore, since prion has recently been reported to be present in platelets, reduction of platelets not only from an erythrocyte preparation but also from a whole blood preparation is regarded to be highly necessary from the viewpoint of reducing a risk of prion infection. Therefore, providing a method for reducing platelets from a blood preparation at a high rate is an urgent issue.

As the method for reducing leukocytes from a cell suspension containing leukocytes, a centrifuge method of reducing leukocytes by centrifuge of the cell suspension, a filter method of filtering the cell suspension through a filter to cause leukocytes to be adsorbed in the filter, a dextran method of adding a physiological saline solution containing dextran to the cell suspension in a blood bag and, after mixing, eliminating a floating leukocyte layer by suction, and the like can be given. Of these, the filter method is widely accepted due to the advantages such as excellent leukocyte reducing capability, simple operation, and a low cost.

JP 03-158168 A describes that the concentration of leukocytes having passed through a fiber laminate exponentially decreases to the thickness of the fiber laminate. This suggests that, when a cell suspension flows in the thickness direction of the fiber laminate, leukocytes are adsorbed at a certain probability every time the leukocytes contact capturing site such as crossing points of the fibers, supporting the above-described adsorption-elimination theory.

For this reason, investigation for promoting performance of leukocyte reducing filters has conventionally been focused on increasing frequency of contact between leukocytes and fibers, specifically, on decreasing the average diameter of fibers, increasing the filling density, or using nonwoven fabrics with a uniform fiber diameter distribution (JP 02-203909 A). Quite a few prior art documents have paid attention to chemical properties on the surface of nonwoven fabrics.

Although excellent leukocyte reducing filters and platelet reducing filters can be obtained by decreasing the average diameter of fibers, increasing the filling density, or using nonwoven fabrics with a uniform fiber diameter distribution, these countermeasures tend to induce bias blood flow, resulting in ineffective performance of the entire filter and fluctuation of leukocyte reduction and platelet reduction. Therefore, improvement of chemical properties on the surface of nonwoven fabrics has been necessary.

Surface modification of nonwoven fabrics by radiation grafting is one of a few studies dealing with chemical properties on the surface of nonwoven fabrics (JP 01-249063 A, JP 03-502094 A, etc.). The surface is reformed with an objective of increasing the platelet permeation rate in JP 01-249063 A, whereas the surface is provided with hydrophilic properties easily to ensure priming with blood in JP 03-502094 A. Thus, neither of the prior art documents has an objective of increasing the adsorption probability of leukocytes, or leukocytes and platelets.

On the other hand, JP 06-247862 A discloses a filter material having basic functional groups and nonionic hydrophilic groups at a molar ratio of the basic functional groups to the nonionic hydrophilic groups of not less than 0.6 to less than 6 and having a content of the basic functional groups of not less than $5 \times 10^{-5}$ meq/m$^2$ to less than 0.1 meq/m$^2$. However, this filter exhibits an insufficient effect of suppressing erythrocyte adhesion, and does not stably ensure the improvement of the leukocyte reduction performance.

WO 87/05812 discloses a filter element coated with an appropriate amount of a polymer having nonionic hydrophilic groups and basic nitrogen-containing functional groups and containing the basic nitrogen-containing functional groups in an amount of not less than 0.2 wt % to less than 4.0 wt %. An example showing superior leukocyte reducing capability and platelet permeability of the filter is presented. WO 87/05812 also presents a comparative example showing increased reduction of both platelets and leukocytes if a polymer containing more basic nitrogen-containing functional groups is used. WO 87/05812, however, concretely describes the treatment with respect to cattle blood only. No specific information about the treatment with respect to human blood is given. Performance of reducing leukocytes and platelets from human blood has not been known. In addition, WO 87/05812 does not disclose any information on the reduction of leukocytes and platelets from an erythrocyte preparation.

The inventors of the present invention have previously prepared a filter for blood processing by coating a filter substrate with a polymer and discovered that the content of low molecular weight components in the polymer relates to the leukocyte reduction rate in human whole blood processing. The inventors have filed an application for patent on a filter for reducing leukocytes from whole blood (Japanese Patent Application No. 2000-099715). However, the invention did not investigate simultaneous reduction of leukocytes and platelets from a whole blood preparation or an erythrocyte preparation.

DISCLOSURE OF THE INVENTION

In view of this situation, the present inventors have conducted extensive studies to develop a filter for blood processing that can reduce leukocytes and platelets from an erythrocyte preparation or a whole blood preparation at the same time at a high reduction rate.

As a result, the inventors have unexpectedly discovered that a filter for blood processing having both high leukocyte reducing performance and high platelet reducing performance can be obtained if a filter substrate is coated with a specific amount of polymer.

This novel finding has led to the completion of the present invention.

Accordingly, a main object of the present invention is to provide a filter for blood processing that can be effectively used for reducing leukocytes and platelets from an erythrocyte preparation or a whole blood preparation at the same time and a process for producing the filter.

The above and other objects, features, and advantages of the present invention will become apparent from the following detailed description and the appended claims given in reference to the attached drawings.

The present invention provides a filter for reducing leukocytes and platelets from an erythrocyte preparation or a whole blood preparation, characterized by having a filter substrate coated with a polymer, the content of the polymer being 0.5–10 mg/m$^2$ per unit area of the total surface of the filter substrate, and the polymer having a molecular weight distribution in which the content of low-molecular weight components having a molecular weight not more than ¼ of the peak top molecular weight in the gel permeation chromatogram is 20% or less.

The basic features and various preferred embodiment of the present invention will now be given for assisting better understanding of the present invention.

The present invention is described below in detail.

The filter of the present invention has a filter substrate coated with a polymer. The polymer has a molecular weight distribution in which the content of low-molecular weight components having a molecular weight not more than ¼ of the peak top molecular weight in the gel permeation chromatogram is 20% or less.

Figure 1:
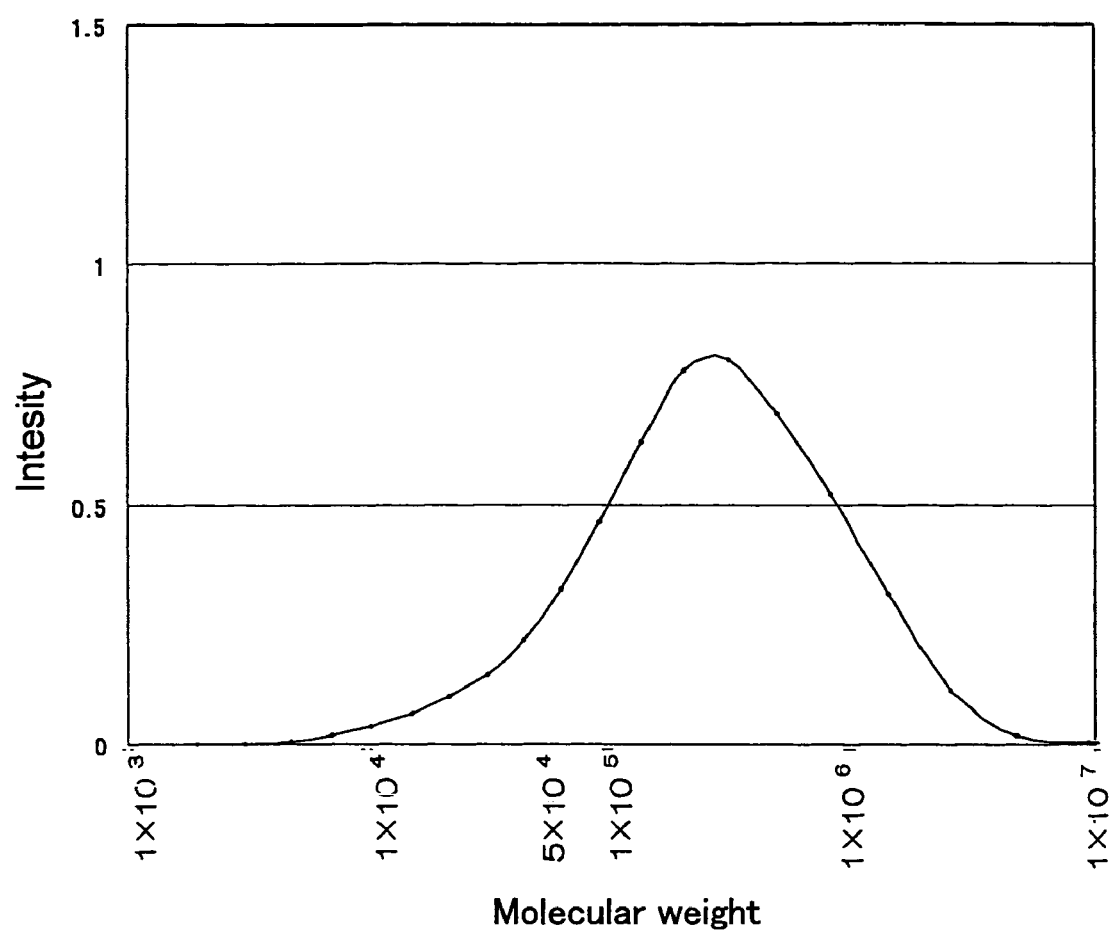
FIG. 1 is a graph showing a molecular weight distribution of the polymer used for preparing the filter for blood processing of the present invention.

The low molecular weight components in the present invention refer to the components having a low polymerization degree, of which the molecular weight is ¼ or less of the peak top molecular weight, namely, the molecular weight of the component having a maximum strength in the gel permeation chromatogram of the polymer (FIG. 1). Dimers, trimers, oligomers and the like can be given as examples of the low molecular weight components.

In the present invention, the 20% or less content of low-molecular weight components having a molecular weight not more than ¼ of the peak top molecular weight in the gel permeation chromatogram refers to that the proportion of the peak area for the components having a molecular weight not more than ¼ of the peak top molecular weight in the gel permeation chromatogram shown in FIG. 1 is 20% or less of the total peak area. In FIG. 1, the horizontal axis represents the molecular weight and vertical axis represents the RI (the intensity measured by a differential refractive index detector).

The molecular weight and molecular weight distribution of polymers are measured by the gel permeation chromatography. Specifically, a solution of a polymer dissolved in a solution (hereinafter referred to as "Solution A") prepared by adding LiBr (lithium bromide) to N,N-dimethylformamide to a concentration of 1 mmol is measured at a temperature of 40° C. by an RI (differential refractive index detector) using gel permeation chromatography (GPC)(main body: HLC-8020, manufactured by Tosoh Corp., Japan+ analytical program: GPC-LALLS Ver. 2.03) connected to a column. The column comprises a guard column (TSK guard column H$_{XL}$-H, manufactured by Tosoh Corp., Japan) and a main column (a fore column: TSK gel GMH$_{XL}$ B0032, manufactured by Tosoh Corp., Japan and a rear column: TSK gel α-M B0011, manufactured by Tosoh Corp., Japan). The measurement is carried out under the condition that the solution A is used for the moving phase and the column temperature is 40° C.

A correlation between a known molecular weight of polymethyl methacrylate (M-M-10 set (manufactured by Polymer Laboratories Inc., UK)) available from GL Sciences Inc. Japan and a value (retention time) measured by GPC of the polymethyl methacrylate was used to determine the molecular weight and molecular weight distribution of the polymers.

The molecular weight and molecular weight distribution of a polymer may be determined prior to coating the filter substrate with the polymer. To determine molecular weight and molecular weight distribution of a polymer in a filter, the polymer may be extracted from the filter before determination.

The polymer can be extracted from the filter by dipping the filter in a solvent that does not dissolve the filter substrate but dissolves the polymer. When the polymer is a copolymer of 2-hydroxyethyl (meth)acrylate and dimethylaminoethyl (meth)acrylate, N,N-dimethylformamide and alcohols such as methanol, ethanol, propanol or the like can be used as the solvent. The extracted polymer is dried to remove the solvent and subjected to the molecular weight distribution determination according to the above-described method.

The polymer used for preparing the filter of the present invention must be refined to reduce low molecular weight components after polymerization by a conventional method.

Conventional methods for removing low molecular weight components from polymers such as a re-precipitation method and fractionation method may be difficult to reduce the content of low-molecular weight components having a molecular weight not more than ¼ of the peak top molecular weight to 20% or less in the gel permeation chromatogram of the polymer.

The method for reducing the amount of low molecular weight components to obtain a polymer with the above-described molecular weight distribution in the present invention includes, but is not limited to, chromatography method, phase separation method or the like. The polymer refining method by phase separation in the present invention refers to a method of separating a polymer solution into a polymer rich layer and a polymer poor layer by thermally induced phase separation and/or non-solvent induced phase separation and selecting and collecting only the polymer rich layer by fractionation.

If a polymer solution is allowed to stand in a vessel for a prescribed period of time after liquid-liquid phase separation, two completely separate layers, which a polymer rich layer with high specific gravity is in the lower layer, can be obtained. Therefore the polymer rich layer can be selected and collected by removing the polymer poor layer in the upper layer or by collecting only the polymer rich layer in the lower layer.

The liquid-liquid phase separation in the present invention refers to an operation of separating a polymer solution homogeneously dissolved at a certain temperature into two liquid layers (a polymer rich layer and a polymer poor layer), each layer having a concentration and molecular weight distribution of the polymer different from those of the other layer. The liquid-liquid phase separation does not include a phase change involving deposition of a solid phase or a solid polymer.

The thermally induced phase separation in the present invention refers to a phase separation of a polymer solution homogeneously dissolved at a certain temperature into multiple layers (for example, liquid-liquid, liquid-solid, or liquid-liquid-solid, etc.) by cooling or heating the polymer solution at a constant rate. Among these, the phase change into liquid-liquid layers is applied to the present invention.

The non-solvent induced phase separation in the present invention refers to a phase separation of a polymer solution homogeneously dissolved at a certain temperature into multiple layers (for example, liquid-liquid, liquid-solid, or liquid-liquid-solid, etc.) by adding a non-solvent to the polymer solution. Among these, the phase change into liquid-liquid layers is applied to the present invention.

When manufacturing a polymer with a particularly high molecular weight, many and various ideas are applied to the manufacturing process to increase the conversion rate of monomers as high as possible. For this reason, polymers with a particularly high molecular weight often have an extremely low content of low molecular weight components. When such a polymer with a particularly high molecular weight is used in the present invention, the polymer may have the above-described molecular weight distribution without being subjected to a particular treatment.

A polymer with a weight average molecular weight of 300,000–3,000,000, preferably 300,000–2,000,000, and more preferably 350,000-2,000,000 is used for coating the filter substrate in the present invention. If the weight average molecular weight is less than 300,000, the amount of materials eluted from the filter of the present invention tends to increase. If the weight average molecular weight is more than 3,000,000, it is difficult for the polymer to be dissolved in a solvent and applied to the filter substrate.

Any polymer swellable and not dissolved in water may be used in the present invention. Examples of such a polymer include, but are not limited to, polymers having a sulfonic acid group, carboxyl group, carbonyl group, amino group, amide group, cyano group, hydroxyl group, methoxy group, phosphoric acid group, oxyethylene group, imino group, imide group, imino ether group, pyridine group, pyrrolidone group, imidazole group, quaternary ammonium group, and the like, either alone or in combination.

A copolymer having a nonionic hydrophilic group and a basic nitrogen-containing functional group among these groups is preferable.

A hydroxyl group, amide group, and the like can be given as the nonionic hydrophilic group in the present invention.

As examples of the monomer having a nonionic hydrophilic group, monomers having the above-described hydroxyl group and amide group, such as 2-hydroxyethyl (meth)acrylate, 2-hydroxypropyl (meth)acrylate, vinyl alcohol (polymerization of vinyl acetate followed by hydrolysis of the polymer), (meth)acrylamide, and N-vinyl pyrrolidone can be given. In addition to the hydroxyl group and amide group, a polyethylene oxide chain can also be given as the nonionic hydrophilic group. As monomers having a polyethylene oxide chain, alkoxy polyethylene glycol (meth) acrylates such as methoxy ethylene glycol (meth)acrylate, methoxy diethylene glycol (meth)acrylate, methoxy triethylene glycol (meth)acrylate, and methoxy tetraethylene glycol (meth)acrylate can be given. Among the above monomers, 2-hydroxyethyl (meth)acrylate is preferably used in view of availability, handling during polymerization, and performance when blood is caused to flow through the filter.

A primary amino group, secondary amino group, tertiary amino group, quaternary ammonium group, and nitrogen-containing aromatic groups such as a pyridine group and imidazole group can be given as the basic nitrogen-containing functional groups, for example.

As monomers having a basic nitrogen-containing functional group, allyl amines; derivatives of (meth)acrylic acid such as dimethylaminoethyl (meth)acrylate, dimethyl aminopropyl (meth)acrylate, 3-dimethylamino-2-hydroxyl (meth)acrylate, and the like; styrene derivatives such as p-dimethylaminomethyl styrene, p-dimethylaminoethyl styrene, and the like; vinyl derivatives of a nitrogen-containing aromatic compound such as 2-vinyl pyridine, 4-vinyl pyridine, 4-vinyl imidazole, and the like; and derivatives such as quaternary ammonium salts prepared by reacting the above vinyl compounds with an alkyl halide or the like can be given. Among the above monomers, dimethylaminoethyl (meth)acrylate and diethylaminoethyl (meth)acrylate are preferably used in view of availability, handling during polymerization, and performance when blood is caused to flow through the filter.

To simultaneously reduce leukocytes and platelets from a whole blood preparation or an erythrocyte preparation, the coating amount of the polymer (mg) for the entire surface area of the filter substrate ($m^2$) is in the range of 0.5–10 mg/$m^2$, and preferably 1–7.5 mg/$m^2$. If the coating amount is less than 0.5 mg/$m^2$, the leukocyte reduction greatly fluctuates; if more than 10 mg/$m^2$, the platelet reduction may decrease to a less than 95% level.

Since platelets induce an isoimmunization response, a standard limiting the number of migrated platelets in erythrocyte preparations to $1.5 \times 10^{10}$/unit or less has been established in the Netherlands and other countries. To sufficiently reduce platelets from a whole blood preparation only by filtration without using centrifuge, 95% or higher reduction rate is required.

The entire surface area ($m^2$) in the present invention refers to a value obtained by multiplying the weight (g) by the specific area ($m^2$/g) of the filter substrate to be coated. The entire surface area thus includes not only the area on the surface of the filter substrate but also the area in the internal pores of the filter substrate. The specific area in the present invention refers to a value determined using "Accusorb 2100E" (manufactured by Shimadzu Corp., Japan) or an instrument with an equivalent specification. After filling a sample tube with 0.50–0.55 g of the filter substrate and deaerating the tube to $1\times10^{-4}$ mmHg (at room temperature) for 20 hours, the specific area is determined using krypton gas as an adsorption gas at an adsorption temperature equivalent to a liquid nitrogen temperature.

The coating amount Y (mg/m$^2$) of the polymer for the entire surface area (m$^2$) of the filter substrate of the present invention can be determined by applying the coating amount X (mg/m$^2$) of the polymer per unit area (m$^2$) of a cut filter substrate, the weight of the substrate per unit area (Metsuke) A (g/m$^2$), and the specific surface area B (mg/m$^2$) of the substrate to the following formula:

$$Y=X/(A\times B)$$

Figure 2:
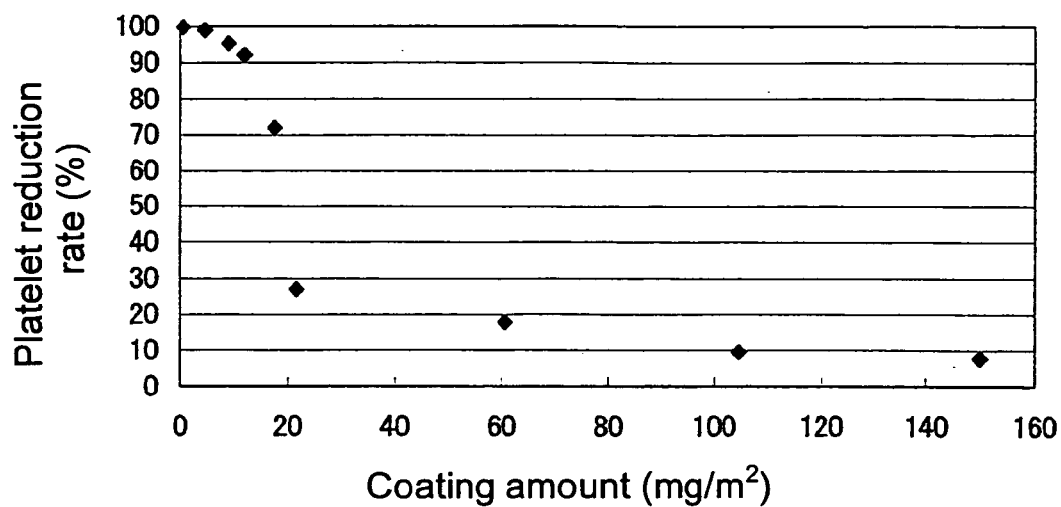
FIG. 2 is a graph showing the relationship between the polymer coating amount of the filter for blood processing of the present invention and the reduction rate of platelet from whole blood.

FIG. 2 shows the results of a test conducted by the inventors of the present invention for determining the correlation between the coating amount of the polymer and the platelet reduction performance from whole blood. In FIG. 2, the rate of platelet reduction from the whole blood is plotted versus the coating amount of the polymer for the entire surface area of the filter substrate (g/m$^2$).

The polymer used in this test was a copolymer of 2-hydroxyethyl (meth)acrylate and dimethylaminoethyl (meth)acrylate, and the substrate was a non-woven fabric (Metsuke: 40 g/m$^2$, void ratio: 79%, thickness: 0.25 mm, specific surface area: 2.01 m$^2$/g) of polyethylene terephthalate fiber with an average fiber diameter of 1.2 μm.

As shown in FIG. 2, the rate of platelet reduction from the whole blood remarkably increases if the coating amount of the polymer is 10 mg/m$^2$ or less.

Figure 3:
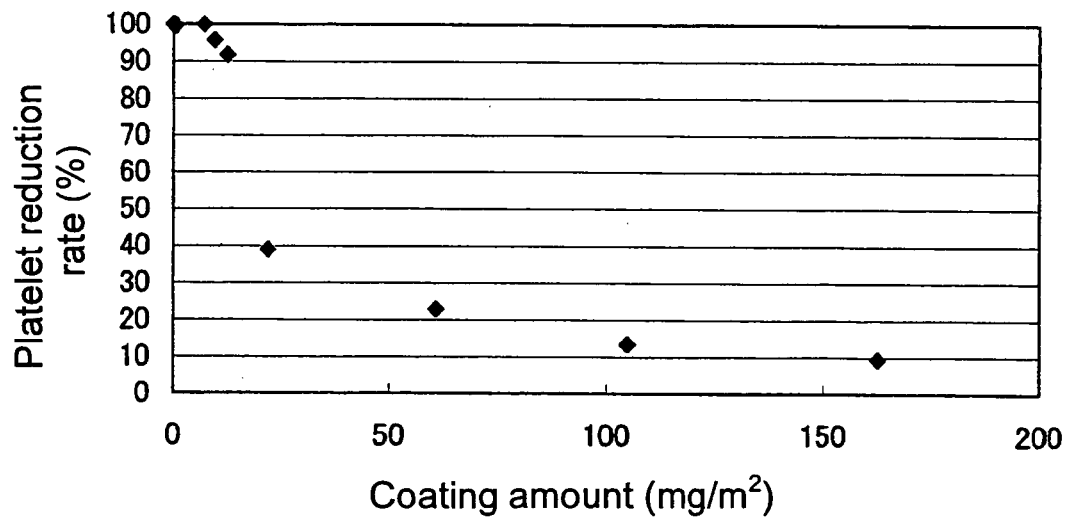
FIG. 3 is a graph showing the relationship between the polymer coating amount of the filter for blood processing of the present invention and the reduction rate of platelet from an erythrocyte preparation.

FIG. 3 shows the results of a test for determining the correlation between the coating amount of the polymer and the platelet reduction performance from an erythrocyte preparation. The same polymer and substrate as used in the above platelet reduction performance test from the whole blood were used. As shown in FIG. 3, the rate of platelet reduction increases as the coating amount of the polymer decreases. It can be seen that the rate of platelet reduction from the erythrocyte preparation also remarkably increases when the coating amount of the polymer decreases to 10 mg/m$^2$ or less.

The specific correlation between the coating amount of the polymer and the rate of platelet reduction shown in FIGS. 2 and 3 has not been known in the past, but has been discovered for the first time by the inventors of the present invention.

The polymer coating ratio for the entire surface of the filter substrate in the present invention is preferably less than 70%. The polymer coating ratio (%) is measured by the X-ray photoelectron spectroscopy (XPS) and can be determined from the amount of the polymer in the covering area of the filter substrate and the amount of the filter substrate.

The polymer coating ratio in the in the present invention refers to the proportion of the area coated with the polymer in the entire surface area of all the elements composing the filter substrate. Since there is no means for accurately measuring the coating ratio in the entire surface area of the filter substrate at the present time, the coating ratio in the entire surface area of the filter is measured by XPS and the resulting value is regarded as a representative value for the coating ratio. The coating ratio of the polymer in the entire surface area of the filter substrate may be less than 70%, and preferably less than 50%. This is an important feature of the present invention. The coating ratio should be less than 70%, and preferably less than 50%, in order to achieve the object of the present invention of providing a filter for processing blood possessing both high leukocyte reducing capability and high platelet reducing capability and capable of being effectively used for reducing leukocytes and platelets from erythrocyte preparations and whole blood. If the coating ratio is 70% or more, the rate of platelet reduction tends to decrease or greatly fluctuate.

Because the rate of platelet reduction increases as the coating ratio decreases, the coating ratio is preferably as small as possible in the present invention.

The reason for the close relationship between the coating ratio and the filter performance, particularly the rate of platelet reduction, is not clear, but can be presumed as follows.

Since there are a number of sites on the surface of the filter substrate on which platelets are easily adsorbed (such sites are hereinafter referred to as "platelet adsorbing sites"), platelets are easily adsorbed in the filter substrate if caused to contact with the filter substrate of which the surface is exposed as large as without being coated with the polymer.

The coating ratio of the filter substrate in the filter for blood processing of the present invention can be measured by the X-ray photoelectron spectroscopy (hereinafter referred to as XPS), conventionally used for measuring chemical conditions on the surface of an object to a depth of 10 Å to 100 Å, using a monochrome X-ray source according the following method.

First, an element or a partial structure by which the existence ratio of the filter substrate to the polymer is most clearly reflected in the XPS spectrum is selected. This element or partial structure is selected taking into consideration the structural difference between the filter substrate and the polymer such as an element which is contained in the filter substrate but not in the polymer and a certain partial structure commonly possessed by the filter substrate and polymer, but at a different ratio.

Then, the XPS spectrums are measured for the standard samples of the filter substrate and the polymer to determine the ratio of the peak area of the element or the partial structure selected above to another specific peak area observed in the XPS spectrum. The ratio determined for the standard sample of the filter substrate and that of the polymer are respectively designated as $X^1$ and $X^2$.

If the surface of the filter substrate is coated with the polymer, the surface of the filter is occupied by the filter substrate and the polymer according to the coating ratio. The existence ratio of the polymer on the surface of the filter increases as the coating ratio increases.

As a result, if the XPS spectrum of the filter surface is measured, the spectra for the mixture of the filter substrate sample and the polymer sample can be obtained. The ratio X of the peak area for the selected element and partial structure to the area of the other specific peak with respect to this filter is between $X^1$ and $X^2$. This is utilized for defining the existence ratio (i.e. coating ratio) of the filter substrate to the coating material (polymer) on the surface of the filter.

The method will now be specifically described taking the filter using polyethylene terephthalate (hereinafter referred to as "PET") as the filter substrate and polyhydroxyethyl methacrylate (hereinafter referred to as "PHEMA") as the polymer.

Both PET and PHEMA are formed from hydrogen, carbon, and oxygen. There is no element contained in either one of the polymers. Therefore, it is impossible to determine the existence ratio of PET and PHEMA using an element contained in either one of the polymers as an index. Therefore, the existence ratio of PET to PHEMA is determined taking into consideration the content of carbon atom of which the state of chemical bonding differs in these polymers.

The carbon atoms forming PET and PHEMA can be classified into the following three types:

a) carbonyl carbon atoms, b) carbon atoms directly bonded to an oxygen atom by a single bond, and c) carbon atoms not directly bonded to an oxygen atom.

The structural unit forming PET includes two carbonyl carbon atoms, two carbon atoms directly bonded to an oxygen atom by a single bond, and six carbon atoms not directly bonded to an oxygen atom.

The structural unit forming PHEMA includes one carbonyl carbon atom, two carbon atoms directly bonded to an oxygen atom by a single bond, and three carbon atoms not directly bonded to an oxygen atom.

The existence ratio (ratio in the number) of the carbon atoms not directly bonded to an oxygen atom to carbonyl carbon atoms is 3:1 in both PET and PHEMA.

The existence ratio (ratio in the number) of the carbon atoms directly bonded to an oxygen atom by a single bond to the carbonyl carbon atoms is 1:1 in PET, whereas that ratio is 2:1 in PHEMA.

The difference of the ratio can be detected as the difference of the ratio of the peak intensity (the peak area) in the XPS spectra.

Specifically, the ratio of the peak intensity (area) for the carbon atoms directly bonded to an oxygen atom by a single bond to the peak intensity (area) for the carbonyl carbon atoms is 1:1 in the XPS spectrum of PET, whereas the corresponding ratio in the XPS spectrum of PHEMA is 2:1.

If the surface of the nonwoven fabric made from PET fiber is coated with PHEMA, the surface of the filter of the present invention is occupied by a mixture of PET and PHEMA according to the coating ratio. The ratio of the PHEMA on the surface of the filter increases as the coating ratio increases. As a result, if the XPS spectrum of the surface of the nonwoven fabric is measured, the spectra of a mixture of PET and PHEMA can be obtained. The ratio of the peak intensity (area) for the carbon atoms directly bonded to an oxygen atom by a single bond to the peak intensity (area) for the carbonyl carbon atoms is between PET and PHEMA. When the coating ratio is 0%, the ratio of the peak intensity (area) is 1:1. The ratio approaches 2:1 as the coating ratio increases and reaches 2:1 when the coating ratio becomes 100%.

This is utilized for defining the coating ratio of the filter of the present invention obtained by coating the surface of the nonwoven fabric made from PET fiber with PHEMA.

Figure 4:
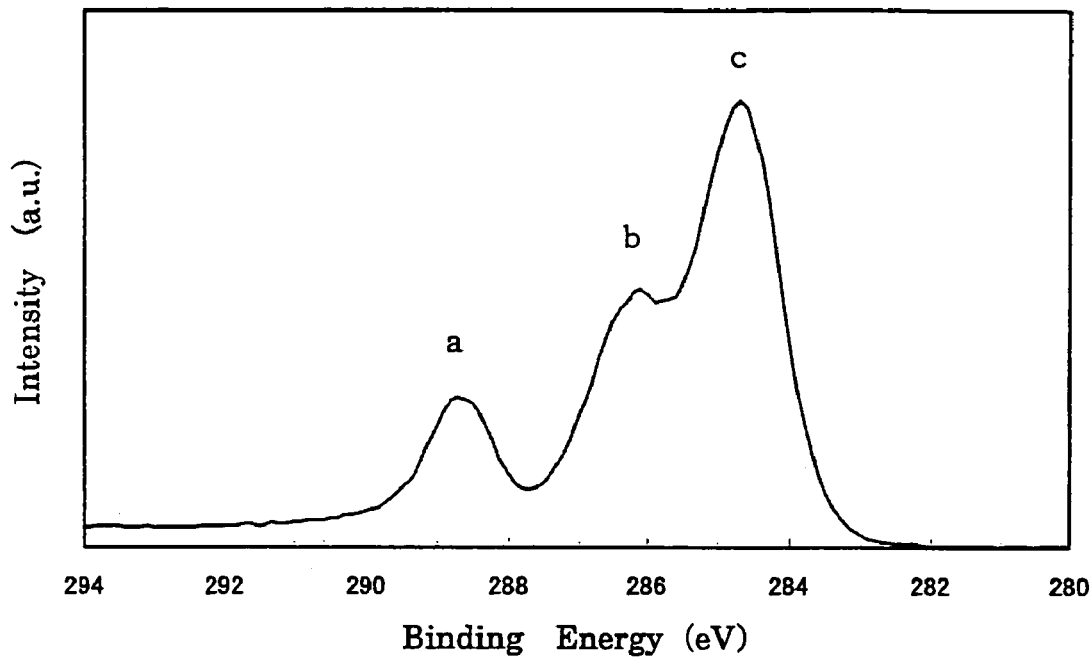
FIG. 4 is an example of X-ray photoelectron spectroscopy (XPS) of the filter for blood processing of the present invention.

PET, PHEMA, and the filter of the present invention have peaks at the positions approximately shown in the XPS spectrum of FIG. 4. In FIG. 4, the peak a is for the carbonyl carbon atoms, the peak b is for the carbon atoms directly bonded to an oxygen atom by a single bond, and the peak c is for the carbon atoms not directly bonded to an oxygen atom.

Assuming that the ratio of area for the peak a to the peak b in the standard PET sample is 1:x, the ratio of areas for the peak a and peak b in the standard PHEMA sample is 1:y, and the ratio of areas for the peak a and peak b in the filter sample is 1:z, the coating ratio of the filter sample can be defined by the following formula:

$$\text{Coating ratio (\%)} = \{|z-x|/|y-x|\} \times 100$$

The coating ratio of the filter with a combination of filter substrate and polymer other than the combination of PET and PHEMA can be also determined in the same manner.

In the present invention the value of a coating ratio determined for the surface of a filter in the above-described manner is taken as the coating ratio of that filter.

It is difficult to obtain a filter with desired performance in the present invention unless not only the filter surface but also the entire surface of the filter substrate elements forming the filter (specifically, the areas inside the filter) is coated with the polymer. Therefore, the following procedure is used to confirm that the filter substrate is uniformly coated inside the filter.

First, the filter is cut through an appropriately selected line on the filter. Next, five points, with respect to each three points of one point close to the surface of one side, another point close to the surface of the other side, and the point at an equivalent distance from the two surfaces, are randomly selected on the cross-section surface to obtain XPS spectrum. The configurations of the obtained XPS spectrum should be confirmed to be equivalent, which means not to be significantly different from each other. The uniformity of coating in the thickness direction is evaluated in this manner.

If the filter is cut, the filter substrate is exposed on the cross-section, giving rise to a significant decrease in the apparent coating ratio on the cross-section. This greatly affects the XPS spectrum and decreases the signal intensity of the polymer in XPS spectrum on the filter cross-section. As a result, the configuration of XPS spectrum on the filter cross-section becomes different from the configuration of XPS spectrum on the filter surface. When comparing the configurations of XPS spectra on the cross-section of each filter, the measuring area must be narrowed, resulting in an increase in noises and making it difficult to obtain distinct XPS spectra. Thus, there is no point in comparing signal intensity ratios (peak area ratios) of these XPS spectra. For this reason, the configurations of XPS spectra are regarded to be equivalent when signals are observed at the same point on the cross-section of each filter, specifically when the chemical shifts for signals observed in each XPS spectrum are identical.

The method for preparing the filter for blood processing of the present invention will now be described.

The filter for blood processing of the present invention can be prepared by a process comprising (1) coating a filter substrate with a solution prepared by dissolving a polymer in a solvent (hereinafter referred to as "polymer solution") or dipping the filter substrate in the polymer solution and (2) removing the excess polymer solution from the filter substrate by means of a mechanical compression, gravity, centrifuge, gas blowing, or vacuum suction, or by dipping in a non-solvent to remove the solvent, followed by drying.

Oxidizing the surface of the filter substrate by γ-ray radiation, UV-ray radiation, corona discharge, or plasma processing, or with chemicals prior to coating is effective for increasing adhesion of the polymer with the filter substrate. It is also possible to treat the filter substrate and the polymer with heat in a gas or liquid after coating, to increase adhesion of the polymer with the filter substrate. A crosslinking reaction in the polymer is also effective to stabilize the coating layer. The filter substrate may be coated either simultaneously with forming the filter substrate or after forming.

As the method for coating the filter substrate with the polymer solution, either a post-measuring method of coating the polymer solution in an amount larger than the desired coating amount and then reducing the amount to a prescribed amount or a pre-measuring method of previously measuring a desired coating amount of the polymer solution and then transferring the solution to the filter substrate can be used.

As the method for drying after coating, a method of drying in dry air, a method of drying under reduced pressure, a method of drying at room temperature, a method of drying with heating, or the like can be used.

Examples of the solvent used for dissolving the polymer, when the polymer is a copolymer of 2-hydroxyethyl (meth) acrylate and dimethylaminoethyl (meth) acrylate, include glycols such as ethylene glycol, and diethylene glycol; alcohols such as methanol, ethanol, n-propyl alcohol, isopropyl alcohol, n-butyl alcohol, and t-butyl alcohol; N,N-dimethyl formamide, and methyl cellosolve. These solvents can be used either individually or in combination of two or more. Mixtures of these solvents and water may also be used.

As the filter substrate for the filter for blood processing of the present invention, in addition to nonwoven fabrics prepared by a melt blow method, flash spinning method, paper milling method, or the like, known filter materials of any form such as paper, woven fabrics, mesh fabrics, and porous polymers can be used. Nonwoven fabrics are particularly preferable. A nonwoven fabric herein refers to a fabric prepared by chemically, thermally, or mechanically combining an aggregation of fibers or threads without weaving or knitting.

As examples of the fiber, synthetic fibers such as polyamide, aromatic polyamide, polyester, polyacrylonitrile, polytrifluorochloroethylene, polystyrene, polymethyl (meth) acrylate, polyethylene, polypropylene, and poly-4-methylpentene, and regenerated fibers such as cellulose and cellulose acetate can be given.

The average fiber diameter of the filter substrate of nonwoven or woven fabrics is 0.3–10 µm, preferably 0.3–3 µm, and more preferably 0.5–1.8 µm. If the average fiber diameter is less than 0.3 µm, the pressure loss when filtering blood may be too large to use the filter in practice; if 10 µm or more, on the other hand, leukocytes may not be sufficiently removed because leukocytes have a reduced chance of contact with the fiber.

The average filter diameter is measured using an electron microscope photograph of the sample collected from a woven or nonwoven fabric forming the filter substrate. The average fiber diameter in the present invention is determined as follows.

A portion deemed to be substantially homogeneous is sampled from the woven or nonwoven fabric forming the filter substrate and photographed using a scanning electron microscope or the like. For sampling, the filter substrate is divided into squares with one side length of 0.5 cm and six squares are randomly sampled. In random sampling, each divided square is numbered and the required number of squares is selected by using a table of random numbers, for example. A photograph in the central part of each sampled square is taken at a magnification of 2,500, from one side (for convenience, hereinafter referred to as A side) for three earlier sampled squares and another side (for convenience, hereinafter referred to as B side) for three later sampled squares. Photographs for the central parts and the neighborhood areas of each sampled square are taken until the total number of fibers taken in the photographs becomes above 100. The diameters of all fibers in the photographs obtained in this manner are measured. The diameter herein refers to the width of fiber in the direction perpendicular to the fiber axis. Then, the average diameter is determined by dividing the sum of the diameters of all measured fibers by the number of the fibers. However, in the case where multiple fibers overlap precluding diameter measurement of a fiber which hides itself behind another fiber, multiple fibers are consolidated into a fiber with a larger diameter due to fusing or else, or there are fibers with remarkably different diameters, for example, the data obtained are excluded. When the average fiber diameter on the A side clearly differs from that on the B side of a certain sample, such a sample cannot be regarded as a single filter substrate. Here, the term "clearly differs" as used for the average fiber diameter indicates that the difference is statistically significant. In such an instance, the A side and the B side are regarded as different filter substrates. After identifying the interface of the both sides, the average fiber diameter for the both sides is separately measured again.

The void ratio of the filter substrate formed from a woven or nonwoven fabric is preferably not less than 50% to less than 95%, and more preferably not less than 70% to less than 90%. If the void ratio is less than 50%, the blood does not flow smoothly; if 95% or more, the filter substrate does not have sufficient mechanical strength. The void ratio is determined as follows. The volume (V) of a sample of the filter substrate cut to have a prescribed area is determined from the dry weight (W1) and thickness measured for the sample. Then, the sample is dipped in purified water to deaerate and the weight (W2) of the hydrated filter substrate is measured. The void ratio is then determined applying the measured values to the following formula, $$\text{Void ratio (\%)} = (W2 - W1) \times 100 / \rho / V$$

wherein $\rho$ indicates the density of purified water.

As examples of the porous polymer, porous polymers made from polyethylene, polypropylene, poly-4-methylpentene, polyvinylformal, polyacrylonitrile, polysulfone, cellulose, cellulose acetate, polyurethane, polyvinylacetal, polyester, polyamide, polyether imide, poly(meth)acrylate, polyvinylidene fluoride, and polyimide can be given.

The porous polymers have an average pore diameter of 1–60 µm, preferably 1–30 µm, and more preferably 1–20 µm. If the average pore diameter is less than 1 µm, a fluid containing leukocytes or platelets such as blood flows with difficulty; if more than 60 µm, leukocytes may not be sufficiently removed because leukocytes have a reduced chance of contact with the porous polymer. The average pore diameter herein may be measured in Porofil liquid (manufactured by Coulter Electronics, Ltd.) using a method conforming to the airflow method described in ASTM F316-86.

The filter for blood processing obtained by the process of the present invention can be used by filling the filter in a conventional suitable container for a filter substrate for blood filtration having a blood outlet and inlet ports.

In the present invention, either one sheet of the filter may be used alone or two or more sheets may be used in piles according to the thickness. The number of piled sheets varies according to conditions of blood filtration. Although the number of sheets is not critical, several to several tens of sheets are used. When the filter substrate is a woven or nonwoven fabric, this filter substrate may be used in combination with the filter substrates made from other fibers in piles.

To efficiently reduce leukocytes and platelets from an erythrocyte preparation or a whole blood preparation using a filter for blood processing in which two or more sheets of filters are piled, a filter (a main filter) made from a material with the smallest pore size or the smallest fiber diameter among the filter substrates is preferably coated with a polymer having a molecular weight distribution, in which the content of low-molecular weight components having a molecular weight not more than ¼ of the peak top molecular weight in the gel permeation chromatogram is 20% or less. It is more preferable that all the filters are coated with such a polymer.

In determining the amount of polymer coated on the filter substrate consisting of combining two or more filter materials with different pore sizes or fiber diameters, a single sheet or multiple sheets of the filter substrate having the same pore size or fiber diameter are measured together, then the coated amount is calculated for each filter substrate having the same pore size or fiber diameter.

When using two or more sheets of different filter substrates in piles, the coated amount of polymer is 0.5–10 mg/m$^2$ for the entire surface of the filter substrate. This requires that the filter substrate with the smallest pore size or fiber diameter (the main filter) be coated with the polymer in an amount of this range.

BEST MODE FOR CARRYING OUT THE INVENTION

The present invention will be described by examples, which should not be construed as limiting the present invention.

(Method of Measuring Coating Ratio)

Various kinds of measurement were performed according to the following procedure.

1) Measurement of the Polymer Coating Ratio on the Surface of the Filter Substrate Samples with a dimension of about 1×1 cm cut from a filter substrate were used for measuring the coating ratio of the polymer on the surface of the filter substrate.

Standard film or plate samples made from PET (polyethylene terephthalate) and standard pellet samples prepared by packing copolymer powders (copolymer of 2-hydroxyethyl (meth)acrylate and dimethylaminoethyl (meth)acrylate or copolymer of 2-hydroxyethyl (meth)acrylate and diethylaminoethyl (meth)acrylate) were provided. The samples were analyzed using an X-ray electronic spectrum (XPS) apparatus (AXIS-Ultra manufactured by Shimadzu Corp., Japan) and an Al Kα monochrome light source (300 W) for the X-ray source under the conditions of a pass energy by narrow scan of 10 eV and an analysis area of 700 μm×300 μm, while neutralizing electrostatic charges.

One example of the narrow scan X-ray photoelectron spectrum showing the correlation between the intensity (a.u.) (angstrom unit) and binding energy (eV) obtained by the above analysis is shown in FIG. 4.

2) Details of Peak Separation

The Eclipse Datasystem Version 2.1 (manufactured by Fisons Surface System, UK) was used as software peak separation.

Procedure 1: The area for peak separation was specified to include three peaks a to c shown in the X-ray photoelectron spectrum of FIG. 4 and the background was removed by the Shirley method.

Procedure 2: Three Gaussian/Lorentzian mixed peaks corresponding to the peaks a (originating from the underlined carbon atom in the O—$\underline{C}$=O bond), b (originating from the underlined carbon atom in the C—$\underline{C}$—O bond), and c (originating from the underlined carbon atom in the C—$\underline{C}$—C bond or the C—$\underline{CH_3}$ bond) were specified. The center, height, half band width, and the Gaussian/Lorentzian mixing ratio of the peaks were used as the parameters for the peak separation.

Procedure 3: The peaks were separated using the minimum Chi-Square method to determine the ratio of the area for the peak a to the area for the peak b. The following conditions were applied to the peak separation:

(1) The difference of the half band width between the peak a and the peak b of the sample was limited within the corresponding value of the standard PET sample ±0.1 eV.

(2) The Gaussian/Lorentzian mixing ratio for the peaks a and b was limited to the range of 0.2–0.5, provided that the Gaussian/Lorentzian mixing ratio for the peak b was (the value for the peak a) ±0.15. The Gaussian/Lorentzian mixing ratio for the peak c was limited to the range of 0.2–0.55.

Procedure 4: Assuming that the ratio of areas for the peak a and the peak b in the standard PET sample is 1:x, the ratio of areas for the peak a and the peak b in the standard polymer sample (pellets made form the polymer powder) is 1:y, and the ratio of areas for the peak a and peak b in the filter sample is 1:z, the coating ratio of the filter sample was determined by the following formula:

$$\text{Coating ratio (\%)} = \{|z-x|/|y-x|\} \times 100$$

Filter samples having a residual solvent content of 1 ppm or less and a thickness of 0.1 mm or more were used for the measurement.

3) Measurement of the Coating Ratio Difference in the Thickness direction of the Filter Substrate Narrow Scan: The coating ratio in the thickness direction was measured in the same manner as in the measurement of the coating ratio on the surface of the filter substrate described in 1) above, except for applying the analytical conditions of a pass energy of 40 eV and an analysis area 27 μmφ were employed.

Five measuring points were randomly selected from a cross-section area near the surface of one side of the filter, a cross-section area near the surface of the other side of the filter, and a cross-section area at an equivalent distance from the two surfaces.

In the following Examples and Comparative Examples, Examples 1-1 to 1-8 and Comparative Examples 1-1 to 1-3 relate to processing of erythrocyte preparations, Examples 2-1 to 2-7 and Comparative Examples 2-1 to 2-4 relate to processing of whole blood preparations, and Reference Examples 1 and 2 relate to a test for eluted materials from polymers.

EXAMPLE 1-1

(Preparation of Polymer Coating Solution)

A copolymer of 97 mol % of 2-hydroxyethyl (meth) acrylate and 3 mol % of dimethylaminoethyl (meth) acrylate (weight average molecular weight: 570,000, basic nitrogen atom content: 0.32 wt %, nonionic hydrophilic group content: 97 mol %, basic nitrogen atom: 3 mol %, peak top molecular weight: 3.75×10$^5$, and low molecular weight components: 26.0%) was provided. Ethanol in four times a volume of the polymer solution (copolymer concentration: 39 wt % in ethanol) was added and the polymer was homogeneously dissolved at 40° C. The solution was allowed to stand for 12 hours at room temperature of 25° C. to separate two liquid phases by means of thermally induced phase separation. The polymer rich layer (copolymer concentration: 31 wt %) was selected and collected.

The polymer rich layer thus obtained was confirmed to dissolve a copolymer of 2-hydroxyethyl (meth)acrylate and dimethylaminoethyl (meth)acrylate (basic nitrogen atom content: 0.32 wt %, nonionic hydrophilic group content: 97 mol %, basic nitrogen atom: 3 mol %, peak top molecular weight: $3.92 \times 10^5$, and low molecular weight components: 14.5%), and to decrease the amount of low molecular weight components in the polymer, through liquid-liquid phase separation refining.

Ethanol was added to the polymer rich layer to dissolve the polymer at 40° C., thereby obtaining a homogeneous polymer solution with a copolymer concentration of 0.06 wt %.

(Coating)

Figure 5:
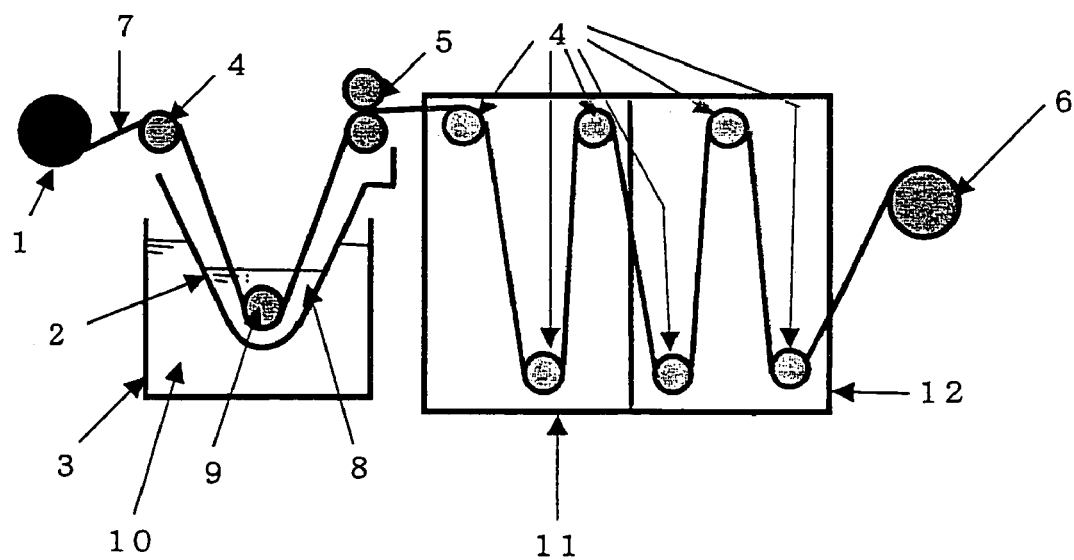
FIG. 5 shows a front elevational view of one embodiment of the device for producing the filter for blood processing of the present invention.

The polymer was coated using the apparatus shown in FIG. 5. Symbols in the FIG. 5 stand for the following items:
1: Filter substrate supply roller
2: Polymer solution coating vessel
3: Thermostat for polymer solution keeping warm
4: Roller
5: Nip roller
6: Roller for rolling up filter
7: Filter substrate
8: Polymer solution
9: Dipping roller
10. Water in thermostat
11: Drying means (low temperature side)
12: Drying means (high temperature side)

A nonwoven fabric (Metsuke: 40 g/m², void ratio: 79%, thickness: 0.25 mm, density: 0.16 g/cm³, width: 300 mm, specific area: 2.01 m²/g, length: 30 m), which was made from polyethylene terephthalate with 1.2 μm of average fiber diameter, was continuously dipped in the above solution at 40° C. using the apparatus shown in FIG. 5 and caused to pass through a clearance of 0.13 mm between the rollers. The nonwoven fabric was caused to pass through a first drying chamber at 40° C. (wind velocity: 15 m/sec) for a length of 3 m and then through a second drying chamber at 60° C. (wind velocity: 15 m/sec) for a length of 3 m, following which the filter was wound around a reel. A fixed line speed of 3 m/min was used. The residual amount of ethanol after passing through the first drying chamber was 11%. The residual amount of ethanol after winding was 1% or less. The filter was efficiently produced with no adhesion among filters after winding. The coating amount on the filter was 0.62 mg/m² and the coating ratio of the polymer was 20%.

(Evaluation of Blood)

An arbitrarily selected part of the filter thus prepared was cut into a number of squares, each having a size of 63 mm×63 mm. 36 square sheets were piled and filled in a container having a blood inlet port and a blood outlet port to a density of about 0.23 g/cm³. The filter had an effective filtering cross-sectional area of 63 mm×63 mm=3,600 mm² and a thickness of 8 mm.

For preparing an erythrocyte preparation, 513 ml of human whole blood (25° C.) consisting of 450 ml of blood and 63 ml of CPD (citrate-phosphate-dextrose) solution was subjected to centrifuge within 8 hours after collection to remove platelet-rich plasma and SAGM (saline-adenine-glucose-mannitol) was added as an erythrocyte preservative. 270 ml of a concentrated erythrocyte preparation (hematocrit 60%) thus obtained was used.

The concentrated erythrocyte preparation was passed through the above filter at a head drop of 70 cm. The blood processing rate during filtration was adjusted to 25 ml/min. Filtration was continued until the blood bag was emptied. The filtered blood was collected.

The leukocyte concentration in the preparation before filtration (prefiltration liquid) and the collected preparation (collected liquid), the volume of the prefiltration liquid, and the volume of the collected liquid were measured to determine the leukocyte reduction rate according to the following formula.

$$\text{Leukocyte reducing capability} = -\text{Log}\left[\frac{\begin{array}{c}\text{leukocyte concentration}\\\text{in collected liquid}\end{array} \times \begin{array}{c}\text{volume of}\\\text{collected liquid}\end{array}}{\begin{array}{c}\text{leukocyte concentration}\\\text{in prefiltration liquid}\end{array} \times \begin{array}{c}\text{volume of}\\\text{prefiltration liquid}\end{array}}\right] \quad (1)$$

The volumes of the prefiltration liquid and the collected liquid were determined by dividing the respective weight by the specific gravity of the blood preparation. The concentrations of leukocytes of the prefiltration liquid and the collected liquid were determined as follows. A TruCOUNT test tube containing a known number of fluorescence beads was charged with 600 μl of the sample liquid. 2,400 μl of LeucoCOUNT reagent was added to the test tube and gently mixed. The mixture was incubated for 5 minutes in a dark place at room temperature. 10 TruCOUNT test tubes adjusted in this manner were continuously measured using a flow site meter (FACSCalibur HG manufactured by Nippon Becton Dickinson Co., Ltd. Japan). A LeucoCOUNT kit (BD-340523, manufactured by Nippon Becton Dickinson Co., Ltd. Japan) was used as the LeucoCOUNT reagent and TruCOUNT test tubes.

Platelet concentrations in the preparations were measured by a multi-item automated hematology analyzer (K-4500, manufactured by Sysmex Corp., Japan) using a stomalizer (manufactured by Sysmex Corp., Japan) as a hemolytic agent. The platelet reduction rate was calculated using the following formula.

$$\text{Platelet reduction rate (\%)} = \left[1 - \frac{\begin{array}{c}\text{Platelet concentration}\\\text{after passing through the filter}\end{array}}{\begin{array}{c}\text{Platelet concentration}\\\text{before passing through the filter}\end{array}}\right] \times 100 \quad (2)$$

The blood evaluation test using the filter was repeated three times, and the results are averaged and shown in Table 1. Leukocyte reducing capability of 5 Log or more is required for a selective leukocyte reducing filter. The results in Table 1 show that the filter has high leukocyte reducing capability.

The filter also showed high platelet reducing capability of a platelet reducing ratio of 95% or more.

EXAMPLE 1-2

An experiment was carried out in the same manner as in Example 1-1, except that a polymer coating solution with a copolymer concentration of 1.25 wt % prepared by adding ethanol to the polymer rich layer of Example 1-1 was used. The coating amount on the filter was 9.55 mg/m$^2$ and the coating ratio of the polymer was 50%.

The results of blood evaluation are shown in Table 1. High leukocyte reducing capability was obtained. The filter also showed high platelet reducing capability of a platelet reducing rate of 95% or more.

EXAMPLE 1-3

An experiment was carried out in the same manner as in Example 1-1 except for using a nonwoven fabric (Metsuke: 40 g/m$^2$, void ratio: 75%, thickness: 0.23 mm, density: 0.17 g/cm$^3$, width: 300 mm, specific area: 1.98 m$^2$/g) made from poly(trimethyleneterephthalate) fiber with 1.2 μm of average fiber diameter, was used instead of the nonwoven fabric used in the Example 1-1. The coating amount on the filter was 0.54 mg/m$^2$ and the coating ratio of the polymer was 20%.

The results of blood evaluation are shown in Table 1. High leukocyte reducing capability was obtained. The filter also showed high platelet reducing capability of a platelet reduction rate of 95% or more.

EXAMPLE 1-4

An experiment was carried out in the same manner as in Example 1-1 except for using a polymer rich layer (copolymer concentration 30 wt %) of a copolymer of 95 mol % of 2-hydroxyethyl (meth) acrylate and 5 mol % of diethylaminoethyl (meth)acrylate (peak top molecular weight: 4.08×10$^5$, low molecular weight components: 9.9%, basic nitrogen atom content: 0.53 wt %, nonionic hydrophilic group content: 95 mol %, basic nitrogen atom: 5 mol %), instead of the polymer rich layer used in Example 1-1. The coating amount on the filter was 0.72 mg/m$^2$ and the coating ratio of the polymer was 20%.

The polymer rich layer of a copolymer of 2-hydroxyethyl (meth)acrylate and diethylaminoethyl (meth)acrylate having a peak top molecular weight of 4.08×10$^5$ and a low molecular weight component content of 9.9% was obtained in the same manner as in Example 1-1 by using a polymer solution (an ethanol solution of copolymer concentration of 41 wt %) containing a copolymer of 95 mol % of 2-hydroxyethyl (meth)acrylate and 5 mol % of diethylaminoethyl (meth) acrylate (weight average molecular weight: 650,000, basic nitrogen atom content: 0.53 wt %, nonionic hydrophilic group content: 95 mol %, basic nitrogen atom: 5 mol %, peak top molecular weight: 3.62×10$^5$, and low molecular weight components: 21.2%). The low molecular weight components in the polymer were confirmed to have decreased during purification by the liquid-liquid phase separation.

The results of blood evaluation are shown in Table 1. High leukocyte reducing capability was obtained. The filter also showed high platelet reducing capability of a platelet reduction rate of 95% or more.

EXAMPLE 1-5

An experiment was carried out in the same manner as in Example 1-1 except for using a polymer rich layer (copolymer concentration 40 wt %) of a copolymer with the same chemical composition as the polymer of Example 1-1 (basic nitrogen atom content: 0.32 wt %, nonionic hydrophilic group content: 97 mol %, basic nitrogen atom: 3 mol %) having a peak top molecular weight of 3.82×10$^5$ and a low molecular weight component content of 12.4%, instead of the polymer rich layer used in Example 1-1. The coating amount on the filter was 0.68 mg/m$^2$ and the coating ratio of the polymer was 20%.

The polymer rich layer of a copolymer of 2-hydroxyethyl (meth)acrylate and dimethylaminoethyl (meth)acrylate having a peak top molecular weight of 3.82×10$^5$ and a low molecular weight component content of 12.4% was obtained by adding a twice volume of ethanol to the polymer solution before purification used in Example 1, homogeneously dissolving the polymer at 40° C., adding n-hexane in an amount (volume) of 0.033 time the amount of the polymer solution dropwise while continuing to mix homogeneously, liquid-liquid phase separating by a non-solvent induced phase separation method and selecting and collecting only the polymer rich layer. The low molecular weight components in the polymer were confirmed to have decreased during purification by the liquid-liquid phase separation.

The results of blood evaluation are shown in Table 1. High leukocyte reducing capability was obtained. The filter also showed high platelet reducing capability of a platelet reduction rate of 95% or more.

EXAMPLE 1-6

An experiment was carried out in the same manner as in Example 1-1 except for using a polymer rich layer (copolymer concentration: 28 wt %) of a copolymer with the same chemical composition as the polymer of Example 1-1 (basic nitrogen atom content: 0.32 wt %, nonionic hydrophilic group content: 97 mol %, basic nitrogen atom: 3 mol %) having a peak top molecular weight of 3.80×10$^5$ and a low molecular weight component content of 18.9%, instead of the polymer rich layer used in Example 1-1. The polymer coating amount on the filter was 0.58 mg/m$^2$ and the coating ratio of the polymer was 20%.

The polymer rich layer of a copolymer of 2-hydroxyethyl (meth)acrylate and dimethylaminoethyl (meth)acrylate having a peak top molecular weight of 3.80×10$^5$ and a low molecular weight component content of 18.9% was obtained by a combination of thermally induced phase separation and non-solvent induced phase separation, which comprises adding a thrice volume of purified water to the polymer solution before purification used in Example 1-1, homogeneously dissolving the polymer at 40° C., allowing the solution to stand for 12 hours at room temperature controlled to 15° C., and selecting and collecting only the polymer rich layer (copolymer concentration: 28 wt %) by liquid-liquid phase separation. The low molecular weight components in the polymer were confirmed to have decreased during purification by the liquid-liquid phase separation.

The results of blood evaluation are shown in Table 2. High leukocyte reducing capability was obtained. The filter also showed high platelet reducing capability of a platelet reduction rate of 95% or more.

COMPARATIVE EXAMPLE 1-1

An experiment was carried out in the same manner as in Example 1-1 except for using a copolymer with the same chemical composition as the polymer of Example 1-4 (basic nitrogen atom content: 0.53 wt %, nonionic hydrophilic group content: 95 mol %, basic nitrogen atom: 5 mol %) having a peak top molecular weight of $3.62 \times 10^5$ and a low molecular weight component content of 20.6%, instead of the polymer rich layer used in Example 1-4.

The results of blood evaluation are shown in Table 2. The polymer coating amount on the filter was 0.50 mg/m$^2$ and the coating ratio of the polymer was 20%.

The copolymer of 2-hydroxyethyl (meth)acrylate and dimethylaminoethyl (meth)acrylate having a peak top molecular weight of $3.62 \times 10^5$ and a low molecular weight component content of 20.6% was obtained by dropping the polymer solution before purification used in Example 1-4 to about a 20-fold volume of purified water portion by portion while homogeneously stirring the solution, re-precipitating the polymer by precipitation, and further drying the precipitate under vacuum at 40° C. The leukocyte reducing capability was lower than 5 Log.

COMPARATIVE EXAMPLE 1-2

An experiment was carried out in the same manner as in Example 1-1, except that a polymer coating solution with a copolymer concentration of 0.04 wt % prepared by adding ethanol to the polymer rich layer of Example 1-1 was used.

The results of blood evaluation are shown in Table 2. Leukocyte reducing capability was evaluated three times to find a significant fluctuation in the leukocyte reducing capability. The average leukocyte reducing capability was lower than 5 Log. The polymer coating amount on the filter was 0.40 mg/m$^2$ and the coating ratio of the polymer was 20%.

Comparative Example 1-3

An experiment was carried out in the same manner as in Example 1-1, except for using a filter substrate on which a polymer is not coated instead of the polymer coated filter used in Example 1-1.

The results of blood evaluation are shown in Table 2. Leukocyte reducing capability was evaluated three times to find a significant fluctuation in the leukocyte reducing capability. The average leukocyte reducing capability was lower than 5 Log.

Example 2-1

The experiment was carried out in the same way as in Example 1-1 except for using whole blood for the evaluation.

Specifically, a filter was produced by coating a polymer coat solution prepared in the same manner as in Example 1-1. In the same manner as in Example 1-1, the content of low molecular weight component was 14.5%, the polymer coating amount on the filter was 0.62 mg/m$^2$, and the coating ratio was 20%. 513 ml of human whole blood consisting of 450 ml of blood and 63 ml of CPD (citrate-phosphate-dextrose) solution was preserved for one day. 270 ml of this blood was filtered and used instead of the erythrocyte preparation. Otherwise, the blood was evaluated in the same manner as in Example 1-1.

The blood evaluation test using the filter was repeated three times, and the results are averaged and shown in Table 3. Leukocyte reducing capability of 5 Log or more was achieved, it was confirmed that the filter demonstrated high leukocyte reducing capability.

Example 2-2

An experiment was carried out in the same manner as in Example 2-1, except that a polymer coating solution with a copolymer concentration of 1.25 wt % prepared by adding ethanol to the polymer rich layer of Example 2-1 was used. The polymer coating amount on the filter was 8.96 mg/m$^2$ and the coating ratio of the polymer was 50%.

The results of blood evaluation are shown in Table 3. High leukocyte reducing capability and high platelet reduction rate were obtained.

Example 2-3

An experiment was carried out in the same manner as in Example 2-1 except for using a nonwoven fabric (Metsuke: 40 g/m$^2$, void ratio: 75%, thickness: 0.23 mm, density: 0.17 g/cm$^3$, width: 300 mm, specific area: 1.98 m$^2$/g) made from poly(trimethyleneterephthalate) fiber with average fiber diameter of 1.2 μm was used instead of the nonwoven fabric used in the Example 2-1. The polymer coating amount on the filter was 0.65 mg/m$^2$ and the coating ratio of the polymer was 20%.

The results of blood evaluation are shown in Table 3. High leukocyte reducing capability and high platelet reduction rate were obtained.

Example 2-4

An experiment was carried out in the same manner as in Example 2-1 except for using a polymer rich layer (copolymer concentration: 29 wt %) of a copolymer of 95 mol % of 2-hydroxyethyl (meth)acrylate and 5 mol % of diethylaminoethyl (meth)acrylate (peak top molecular weight: $4.08 \times 10^5$, low molecular weight components: 9.9%, basic nitrogen atom content: 0.53 wt %, nonionic hydrophilic group content: 95 mol %, basic nitrogen atom: 5 mol %), instead of the polymer rich layer used in Example 2-1. The polymer coating amount on the filter was 0.60 mg/m$^2$ and the coating ratio of the polymer was 20%.

The results of blood evaluation are shown in Table 3. High leukocyte reducing capability and platelet reduction rate were obtained.

Example 2-5

An experiment was carried out in the same manner as in Example 2-1 except for using a polymer rich layer (copolymer concentration 40 wt %) of a copolymer with the same chemical composition as the polymer of Example 1-1 (basic nitrogen atom content: 0.32 wt %, nonionic hydrophilic group content: 97 mol %, basic nitrogen atom: 3 mol %) having a peak top molecular weight of $3.82 \times 10^5$ and a low molecular weight component content of 12.4%, instead of the polymer rich layer used in Example 2-1. The polymer coating amount on the filter was 0.68 mg/m$^2$ and the coating ratio of the polymer was 50%.

The results of blood evaluation are shown in Table 3. High leukocyte reducing capability and high platelet reduction rate were obtained.

Example 2-6

An experiment was carried out in the same manner as in Example 2-1 except for using a polymer rich layer (copolymer concentration: 28 wt %) of a copolymer with the same chemical composition as the polymer of Example 1-1 (basic nitrogen atom content: 0.32 wt %, nonionic hydrophilic group content: 97 mol %, basic nitrogen atom: 3 mol %) having a peak top molecular weight of $3.80 \times 10^5$ and a low molecular weight component content of 12.9%, instead of the polymer rich layer used in Example 2-1. The polymer coating amount on the filter was 0.62 mg/m$^2$ and the coating ratio of the polymer was 20%.

The results of blood evaluation are shown in Table 4. High leukocyte reducing capability and high platelet reduction rate were obtained.

Example 2-7

An experiment was carried out in the same manner as in Example 2-1, except that a polymer coating solution with a copolymer concentration of 0.50 wt % prepared by adding ethanol to the polymer rich layer of Example 2-1 was used. The polymer coating amount on the filter was 4.58 mg/m$^2$ and the coating ratio of the polymer was 40%.

The results of blood evaluation are shown in Table 4. High leukocyte reducing capability and high platelet reduction rate were obtained.

Comparative Example 2-1

An experiment was carried out in the same manner as in Example 2-1 except for using a copolymer with the same chemical composition as the copolymer of Example 1-1 (basic nitrogen atom content: 0.53 wt %, nonionic hydrophilic group content: 97 mol %, basic nitrogen atom: 5 mol %) having a peak top molecular weight of $3.62 \times 10^5$ and a low molecular weight component content of 20.6%, instead of the polymer rich layer used in Example 2-1. The polymer coating amount on the filter was 0.58 mg/m$^2$ and the coating ratio of the polymer was 20%.

The results of blood evaluation are shown in Table 4. Blood evaluation was performed three times to find a significant fluctuation in the platelet reduction rate. The average platelet reduction rate was lower than 95%.

Comparative Example 2-2

An experiment was carried out in the same manner as in Example 2-1, except that a polymer coating solution with a copolymer concentration of 0.04 wt % prepared by adding ethanol to the polymer rich layer of Example 2-1 was used. The results of blood evaluation are shown in Table 4. Leukocyte reducing capability was evaluated three times to find a significant fluctuation in the leukocyte reduction rate. The average leukocyte reduction rate was lower than 5 Log. The polymer coating amount on the filter was 0.40 mg/m$^2$ and the coating ratio of the polymer was 20%.

Comparative Example 2-3

An experiment was carried out in the same manner as in Example 2-1, except for using a filter substrate material on which a polymer is not coated instead of the polymer coated filter used in Example 2-1. The results of blood evaluation are shown in Table 4. Leukocyte reducing capability was evaluated three times to find a significant fluctuation in the leukocyte reducing capability. The average leukocyte reducing capability was lower than 5 Log.

TABLE 1

|  | Example 1-1 | Example 1-2 | Example 1-3 | Example 1-4 | Example 1-5 |
|---|---|---|---|---|---|
| Leukocyte reducing capability | 5.0 | 5.2 | 5.0 | 5.1 | 5.1 |
| Platelet reduction rate (%) | 99.8 | 95.8 | 99.8 | 99.8 | 99.9 |

TABLE 2

|  | Example 1-6 | Comparative Example 1-1 | Comparative Example 1-2 | Comparative Example 1-3 |
|---|---|---|---|---|
| Leukocyte reducing capability | 5.0 | 4.9 | 4.8 | 4.2 |
| Platelet reduction rate (%) | 99.7 | 92.0 | 99.9 | 98.6 |

TABLE 3

|  | Example 2-1 | Example 2-2 | Example 2-3 | Example 2-4 | Example 2-5 |
|---|---|---|---|---|---|
| Leukocyte reducing capability | 5.2 | 5.4 | 5.1 | 5.0 | 5.1 |
| Platelet reduction rate (%) | 99.9 | 95.2 | 99.9 | 99.9 | 99.7 |

TABLE 4

|  | Example 2-6 | Example 2-7 | Comparative Example 2-1 | Comparative Example 2-2 | Comparative Example 2-3 |
|---|---|---|---|---|---|
| Leukocyte reducing capability | 5.0 | 5.3 | 5.0 | 4.8 | 4.1 |
| Platelet reduction rate (%) | 99.0 | 99.0 | 93.2 | 99.6 | 98.4 |

Reference Example 1

A filter with a coating in the amount of 73 mg/m² was obtained in the same manner as in Example 1-4 except for using a polymer coat solution with a copolymer concentration of 3 wt %. The filter obtained was evaluated according to the elution test for rubber materials described in the standard for sterilized blood transfusion sets (Ministry of Health and Welfare, Pharmaceutical and Food Safety Bureau, No. 1079, Dec. 11, 1998). As a result, the filter exhibited potassium permanganate reduction in terms of a consumption difference of 0.21 ml and volatilization residue of 0.05 mg.

Reference Example 2

A filter with a coating in the amount of 71 mg/m² was obtained in the same manner as in Reference Example 1 except for using the polymer used in Comparative Example 1-1. As a result of the same elution test, the filter exhibited potassium permanganate reduction in terms of a consumption difference of 0.36 ml and volatilization residue of 0.20 mg.

The results of Reference Examples 1 and 2 show that the filter of the present invention is more safe due to a smaller amount of elution.

INDUSTRIAL APPLICABILITY

Using the filter for blood processing of the present invention, leukocytes and platelets causing various side effects after transfusion can be efficiently and selectively reduced from an erythrocyte preparation or whole blood preparation while preventing a loss of blood plasma and erythrocytes. The filter for blood processing of the present invention can be used with an extreme advantage in manufacturing the blood preparation for pharmaceutical application, medical application, and general industrial application.

The invention claimed is:

1. A filter for reducing leukocytes and platelets from an erythrocyte preparation or a whole blood preparation, comprising a filter substrate coated with a polymer, the content of the polymer being 0.5–10 mg/m² per unit area of the total surface of the filter substrate, and the polymer having a molecular weight distribution in which the content of components having a molecular weight not more than ¼ of the peak top molecular weight in the gel permeation chromatogram is 20% or less, wherein the polymer coating ratio in the entire surface of the filter substrate is less than 70%, wherein the polymer has a weight average molecular weight of 300,000–3,000,000, and wherein the polymer is swellable and not dissolved in water.

2. The filter according to claim 1, wherein the polymer has nonionic hydrophilic groups and basic nitrogen-containing functional groups.

3. The filter according to claim 2, wherein the filter substrate is a thermoplastic polymer.

4. The filter according to claim 2, wherein the filter substrate is a nonwoven fabric.

5. The filter according to claim 1, wherein the filter substrate is a thermoplastic polymer.

6. The filter according to claim 5, wherein the filter substrate is a nonwoven fabric.

7. The filter according to claim 1, wherein the filter substrate is a nonwoven fabric.

8. A process for producing the filter according to claim 1, comprising
providing a polymer solution of a polymer mixture which contains unreacted monomers and polymers having a molecular weight not more than ¼ of the peak top molecular weight in the gel permeation chromatogram in one or more solvents,
separating the polymer solution in a liquid-liquid phase into a polymer rich layer and a polymer poor layer by thermally induced phase separation and/or non-solvent induced phase separation wherein the polymer rich layer has the polymer having a molecular weight distribution in which the content of components having a molecular weight not more than ¼ of the peak top molecular weight in the gel permeation chromatogram is 20% or less,
diluting the polymer rich layer selectively collected with a solvent, to form a prepared polymer solution and
coating a filter substrate with the prepared polymer solution from the polymer rich layer wherein the polymer coating ratio in the entire surface of the filter substrate is less than 70%, wherein the polymer has a weight average molecular weight of 300,000–3,000,000, and wherein the polymer is swellable and not dissolved in water.

* * * * *